(12) United States Patent
Harrison et al.

(10) Patent No.: US 11,282,193 B2
(45) Date of Patent: Mar. 22, 2022

(54) SYSTEMS AND METHODS FOR TUMOR CHARACTERIZATION

(71) Applicant: PING AN TECHNOLOGY (SHENZHEN) CO., LTD., Shenzhen (CN)

(72) Inventors: Adam P. Harrison, Bethesda, MD (US); Yuankai Huo, Bethesda, MD (US); Jinzheng Cai, Bethesda, MD (US); Ashwin Raju, Bethesda, MD (US); Ke Yan, Bethesda, MD (US); Le Lu, Bethesda, MD (US)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 182 days.

(21) Appl. No.: 16/836,855

(22) Filed: Mar. 31, 2020

(65) Prior Publication Data

US 2021/0304403 A1   Sep. 30, 2021

(51) Int. Cl.
*G06T 7/00* (2017.01)
*G06K 9/62* (2022.01)
(Continued)

(52) U.S. Cl.
CPC ............ *G06T 7/0012* (2013.01); *A61B 6/032* (2013.01); *A61B 6/5217* (2013.01);
(Continued)

(58) Field of Classification Search
None
See application file for complete search history.

(56) References Cited

U.S. PATENT DOCUMENTS

| 2014/0201126 A1* | 7/2014 | Zadeh | A61B 5/165 706/52 |
| 2018/0315188 A1* | 11/2018 | Tegzes | G06K 9/2054 |
| 2018/0353148 A1* | 12/2018 | Smith | G06T 11/005 |

FOREIGN PATENT DOCUMENTS

CN   107818821 A  *  3/2018   ......... G06T 7/0012

OTHER PUBLICATIONS

Choi SH, Lee SS, Kim SY, Park SH, Park SH, Kim KM, Hong SM, Yu E, Lee MG. Intrahepatic Cholangiocarcinoma in Patients with Cirrhosis: Differentiation from Hepatocellular Carcinoma by Using Gadoxetic Acid-enhanced MR Imaging and Dynamic CT. Radiology. Mar. 2017;282(3):771-781. (Year: 2017).*

(Continued)

*Primary Examiner* — Vu Le
*Assistant Examiner* — Courtney Joan Nelson
(74) *Attorney, Agent, or Firm* — Bayes PLLC

(57) ABSTRACT

Systems and methods for characterizing a region of interest (ROI) in a medical image are provided. An exemplary system may include a memory storing instructions and at least one processor communicatively coupled to the memory to execute the instructions which, when executed by the processor, may cause the processor to perform operations. The operations may include detecting one or more candidate ROIs from the medical image using a three-dimensional (3D) machine learning network. The operations may also include determining a key slice for each candidate ROI. The operations may further include selecting a primary ROI from the one or more candidate ROIs based on the respective key slices. In addition, the operations may include classifying the primary ROI into one of a plurality of categories using a texture-based classifier based on the key slice corresponding to the primary ROI.

20 Claims, 13 Drawing Sheets

(51) Int. Cl.
  *G06T 7/49*   (2017.01)
  *A61B 6/03*   (2006.01)
  *A61B 6/00*   (2006.01)

(52) U.S. Cl.
  CPC .............. *G06K 9/6267* (2013.01); *G06T 7/49*
     (2017.01); *G06T 2207/10072* (2013.01); *G06T*
       *2207/20081* (2013.01); *G06T 2207/30096*
                                     (2013.01)

(56) References Cited

OTHER PUBLICATIONS

Machine translation of CN 107818821 (Year: 2018).*
Cheng Jin, Jianjiang Feng, Lei Wang, Heng Yu, Jiang Liu, Jiwen Lu, Jie Zhou, Left atrial appendage segmentation and quantitative assisted diagnosis of atrial fibrillation based on fusion of temporal-spatial information, Computers in Biology and Medicine, vol. 96, 2018, pp. 52-68 (Year: 2018).*
J. Yu, C. Zhu, J. Zhang, Q. Huang and D. Tao, "Spatial Pyramid-Enhanced NetVLAD With Weighted Triplet Loss for Place Recognition," in IEEE Transactions on Neural Networks and Learning Systems, vol. 31, No. 2, pp. 661-674, Feb. 2020, doi: 10.1109/TNNLS.2019.2908982 (Year: 2020).*

\* cited by examiner

SYSTEMS AND METHODS FOR TUMOR CHARACTERIZATION

TECHNICAL FIELD

The present application relates to medical imaging-based tumor diagnosis technologies, and more particularly, to tumor characterization using a fully automated approach based on spatially adaptive texture analyses.

BACKGROUND

Effective and non-invasive tumor characterization from medical imaging has been a major aim in oncology diagnosis and treatment to reduce unnecessary invasive surgical biopsies, which can lead to complications or even patient death. In many cases, correctly characterizing tumors (e.g., identifying the correct type of the tumors) are crucial to the success of treatment, as treatment strategies vary widely among different tumor types.

Advances in medical imaging technologies make it possible to non-invasively diagnose many types of tumors based on clinical information coupled with various imaging modalities, such as ultrasound imaging, magnetic resonance imaging (MRI), and computed tomography (CT), among which CT is perhaps the most common choice due to its cost effectiveness and high fidelity. However, state-of-the-art medical imaging-based diagnoses still face many challenges, such as a high rate of false positives and a high degree of uncertainty, which significantly limit the benefits of diagnosing tumors non-invasively. For example, some medical imaging-based diagnoses may yield uncertain results, and therefore invasive procedures, such as biopsies or surgery, may still be required, which may lead to unpredictable hemorrhage, infections, or even death. Thus, improved non-invasive tumor characterization based on medical imaging is a crucial aim within the medical imaging analysis community.

Medical imaging-based tumor characterization is particularly challenging in diagnosing liver cancer, which is one of the most fatal types of cancer in the world. This is partly because distinguishing different types of liver tumors based on medical images is very challenging. For example, benign and intrahepatic cholangiocarcinomas (ICC) tumors can be misinterpreted as hepatocellular carcinoma (HCC), with separating HCC from hemangioma being a particularly pernicious difficulty. Solitary liver metastases are also difficult to differentiate from ICC. FIG. 13 shows several typical misdiagnosis scenarios. In FIG. 13, multi-phase CT images of patient livers are shown with tumors indicated in boxes. In each row, from left to right, the images are non-contrast (NC), arterial (A), venous (V), and delayed (D) phase CT images, respectively. The top row shows that a benign tumor, in particular, a focal nodular hyperplasia (FNH), is misdiagnosed as an HCC, a malignant tumor. The middle row shows that a hemangioma, another type of benign tumor, is misdiagnosed as an HCC. The bottom row shows that a metastasis, a malignant tumor, is misdiagnosed as an ICC. Such misdiagnoses happen despite the fact that clinical diagnoses from multi-phase CTs are usually performed through consensus between radiologists and clinicians. In medical imaging-based liver cancer diagnosis, false positive rate is quite high. For example, as high as 20% of the patients receiving a liver transplant to treat image-determined HCC in fact had benign tumors.

Embodiments of the disclosure provide improved systems and methods for tumor characterization to address or alleviate the above-discussed issues.

SUMMARY

In one aspect, a system for characterizing a region of interest (ROI) in a medical image is provided. The system may include a memory storing computer-readable instructions and at least one processor communicatively coupled to the memory to execute the computer-readable instructions. The computer-readable instructions, when executed by the at least one processor, may cause the at least one processor to perform operations. The operations may include detecting one or more candidate ROIs from the medical image using a three-dimensional (3D) machine learning network. The operations may also include determining a key slice for each candidate ROI. The operations may further include selecting a primary ROI from the one or more candidate ROIs based on the respective key slices. In addition, the operations may include classifying the primary ROI into one of a plurality of categories using a texture-based classifier based on the key slice corresponding to the primary ROI.

In another aspect, a method for characterizing an ROI in a medical image is provided. The method may include detecting, by a processor, one or more candidate ROIs from the medical image using a 3D machine learning network. The method may also include determining, by the processor, a key slice for each candidate ROI. The method may further include selecting, by the processor, a primary ROI from the one or more candidate ROIs based on the respective key slices. In addition, the method may include classifying, by the processor, the primary ROI into one of a plurality of categories using a texture-based classifier based on the key slice corresponding to the primary ROI.

In a further aspect, a non-transitory computer-readable medium is provided. The non-transitory computer-readable medium may store instructions that, when executed by at least one processor, cause the at least one processor to perform a method for characterizing an ROI in a medical image. The method may include detecting one or more candidate ROIs from the medical image using a 3D machine learning network. The method may also include determining a key slice for each candidate ROI. The method may further include selecting a primary ROI from the one or more candidate ROIs based on the respective key slices. In addition, the method may include classifying the primary ROI into one of a plurality of categories using a texture-based classifier based on the key slice corresponding to the primary ROI.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated herein and form a part of the specification, illustrate embodiments of the present disclosure and, together with the description, further serve to explain the principles of the present disclosure and to enable a person skilled in the pertinent art to make and use the present disclosure.

DETAILED DESCRIPTION

Reference will now be made in detail to the exemplary embodiments, examples of which are illustrated in the accompanying drawings. Wherever possible, the same reference numbers will be used throughout the drawings to refer to the same or like parts.

Embodiments of the present disclosure provide systems and methods for characterizing a region of interest (ROI) in a medical image. An ROI may include a tumor, a lesion, a tissue, an organ, or any part of a human body that is subject to medical diagnosis based on one or more medial images containing the ROI. In this disclosure, the terms "tumor" and "lesion" are used interchangeably, referring to an abnormal mass of tissue that results when cells divide more than they should or do not die when they should. Tumors may be benign (non-cancerous), or malignant (cancerous). ROI (e.g., tumor) characterization may include classifying an ROI into one of several types or categories. For example, liver tumors may include four categories: benign, HCC, ICC, and metastasis. Accordingly, characterizing a liver tumor may include classifying the liver tumor into one of the four categories. In the following description, embodiments of the present disclosure are described in the context of liver tumor characterization. However, it is understood that systems and methods disclosed herein are also applicable to characterizing other types of tumors or ROIs in general.

Embodiments of the present disclosure provide novel and scalable medical imaging-based tumor diagnosis systems and methods using multi-phase CT scans. An exemplary system for tumor characterization can perform fully automated 3D tumor site detection to identify and locate candidate tumors, perform key slice filtering (KSF) to select a two-dimensional (2D) key slice in each candidate tumors, perform primary tumor selection based on the key slices, and classify the selected primary tumor into one of several categories based on the key slice corresponding to the primary tumor using a spatially adaptive deep texture (SaDT) classifier. A semi-automated data curation system is also provided to harvest large-scale unlabeled 3D medical image data with pathology confirmed liver tumors. The curated data can then be used to train various machine learning networks in the tumor characterization system to improve their performance. Unlike existing tumor characterization systems that rely on a limited amount of manually drawn tumor ground truth data for model training, the data curation system provided in this disclosure greatly expands the space of the training data, thereby providing more reliable and more accurate learning models. This end-to-end tumor characterization solution incorporates effective data curation, 3D detection, primary tumor selection, and principled deep texture learning to tackle some of the most challenging tumor characterization tasks within the clinic.

Figure 1:
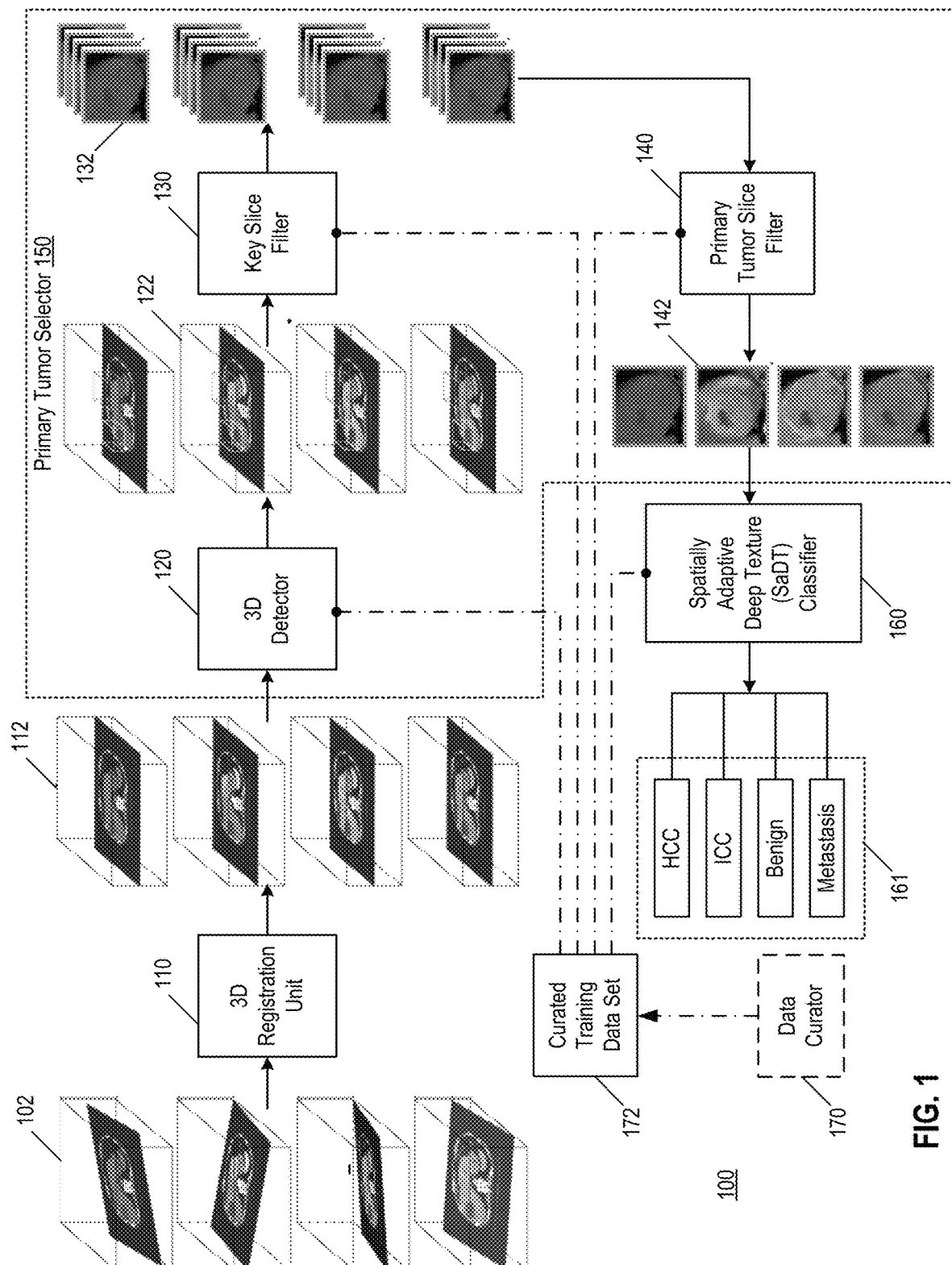
FIG. 1 illustrates an exemplary tumor characterization system, according to embodiments of the disclosure.

FIG. 1 illustrates an exemplary tumor characterization system 100, according to embodiments of the disclosure. System 100 may include a pre-processing stage, in which a 3D registration unit 110 can perform 3D registration of multiple medical images of the same patient. Tumor characterization may then be performed by system 100 in two main stages. The first stage, performed by a primary tumor selector 150, is for determining a primary tumor and its key slice(s). The second stage, performed by an SaDT classifier, is for classifying the primary tumor into one of multiple categories (e.g., HCC, ICC, benign, and metastasis) based on the key slice(s). Primary tumor selector 150 may further include a 3D detector, a key slice filter 130, and a primary tumor slice filter 140. These components of primary tumor selector 150, along with SaDT classifier 160, may be implemented using trainable machine learning networks (also referred to as models), which can be trained from a curated training data set 172 harvested by a data curator 170 from large-scale medical image data.

System 100 will hereinafter be described in the context of a liver tumor characterization workflow or pipeline. As noted above, system 100 is not limited to characterizing liver tumors. Any ROIs subject to medical diagnosis can be characterized by system 100 in a similar manner.

Figure 4:
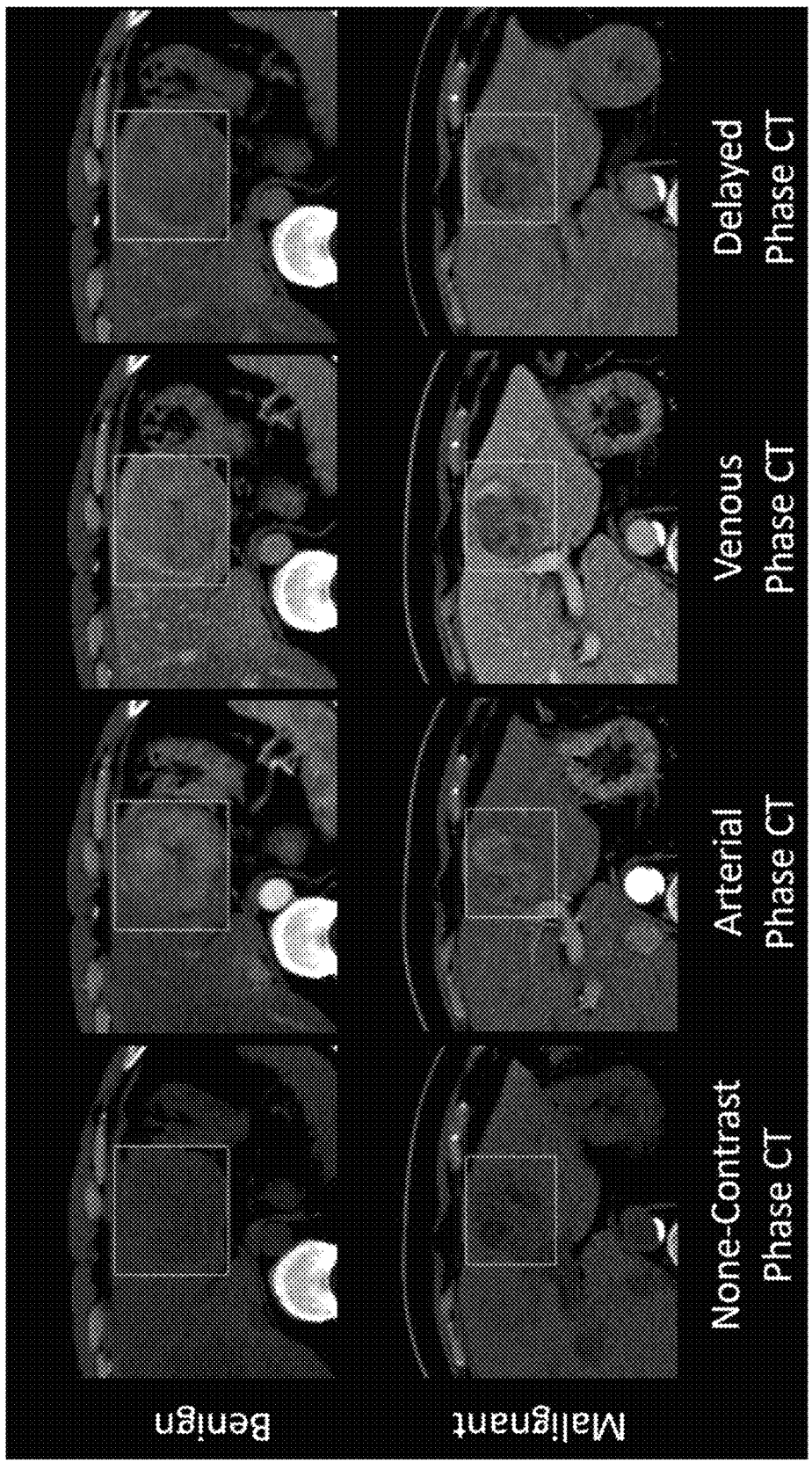
FIG. 4 illustrates exemplary multi-phase CT images from which tumor characterization can be performed, according to embodiments of the disclosure.

As shown in FIG. 1, 3D registration unit 110 may be configured to register medical images 102 of the same patient together to generate 3D medical images 112. Medial images 102 may also be referred to as testing or diagnostic data. Examples of such images include CT scan images. Dense displacement sampling (DEEDS) may be used to register such images. CT scan images 102 may be multi-phase CT images. Multi-phase CT images may include CT images obtained at different time points. For example, FIG. 4 shows exemplary multi-phase CT images of livers. Referring to FIG. 4, from left to right, the four columns of images are obtained at none-contrast phase (e.g., imaging without application of a contrast agent), arterial phase (e.g., when the contrast agent is passing through the arteries), venous phase (e.g., when the contrast agent is passing through the portal veins), and delayed phase (e.g., post-contrast phase). Returning to FIG. 1, after registration, 3D medical images 112 may be processed by primary tumor selector 150, as will be described in greater detail below. It is noted that 3D registration unit 110 may be omitted in some embodiments when, for example, 3D medical images feasible for being processed by primary tumor selector 150 are already available or can be obtained in other ways. Therefore, the 3D registration stage may act as a pre-processing stage for tumor characterization and may or may not be performed depending on particular applications.

Figure 5:
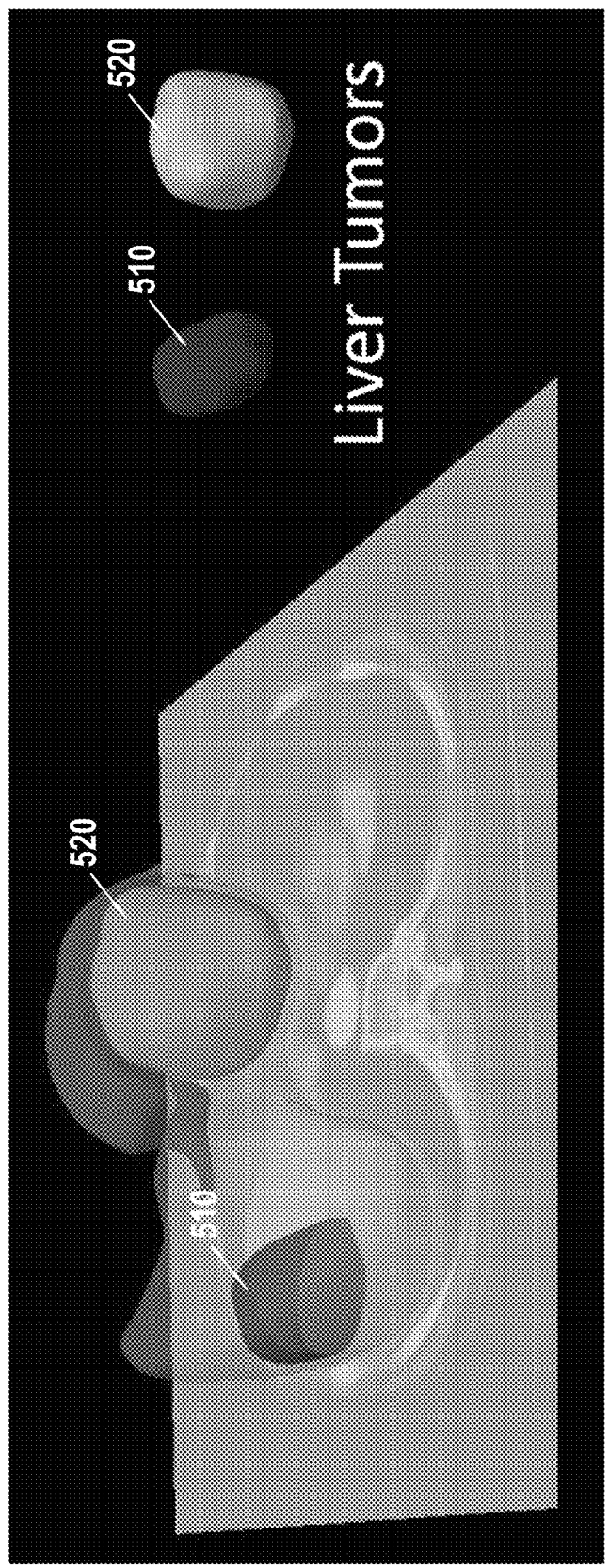
FIG. 5 illustrates exemplary 3D images of liver tumors that can be characterized by the tumor characterization system shown in FIG. 1, according to embodiments of the disclosure.

With the availability of 3D medical images 112, primary tumor selector 150 may determine a primary tumor from 3D medical images 112 and also determine one or more key slices of the primary tumor. A primary tumor may refer to a tumor or a portion of the tumor that has the greatest diagnostical significance when one or more candidate tumors are present in 3D medical images 112. In some cases, the image of the primary tumor may have the largest volume (e.g., in 3D) or the largest area (e.g., in a 2D cross-section). In some cases, the primary tumor may have certain feature(s) that most closely resemble a reference. The criteria for defining the primary tumor may vary. For example, FIG. 5 illustrates exemplary 3D images of liver tumors 510 and 520. Primary tumor selector 150 may determine that, for example, tumor 520 is the primary tumor due to its larger volume and/or better reference-matching features, while tumor 510 is a non-primary tumor. Accordingly, tumor 520 may be selected for characterization purposes. In some embodiments, more than one primary tumor may be selected by primary tumor selector 150 when they all satisfy the criteria (e.g., exceed a certain threshold of volume, feature matching rate, etc.). Returning to FIG. 1, a key slice refers to a 2D slice that contains the representative features of a primary tumor. When multi-phase CT images are used, a key slice may be determined for each phase. As a result, multiple key slices may be determined for a primary tumor. The output of primary tumor selector 150 may include key slice(s) 142 of the selected primary tumor for SaDT classifier 160 to perform classification.

Figure 6:
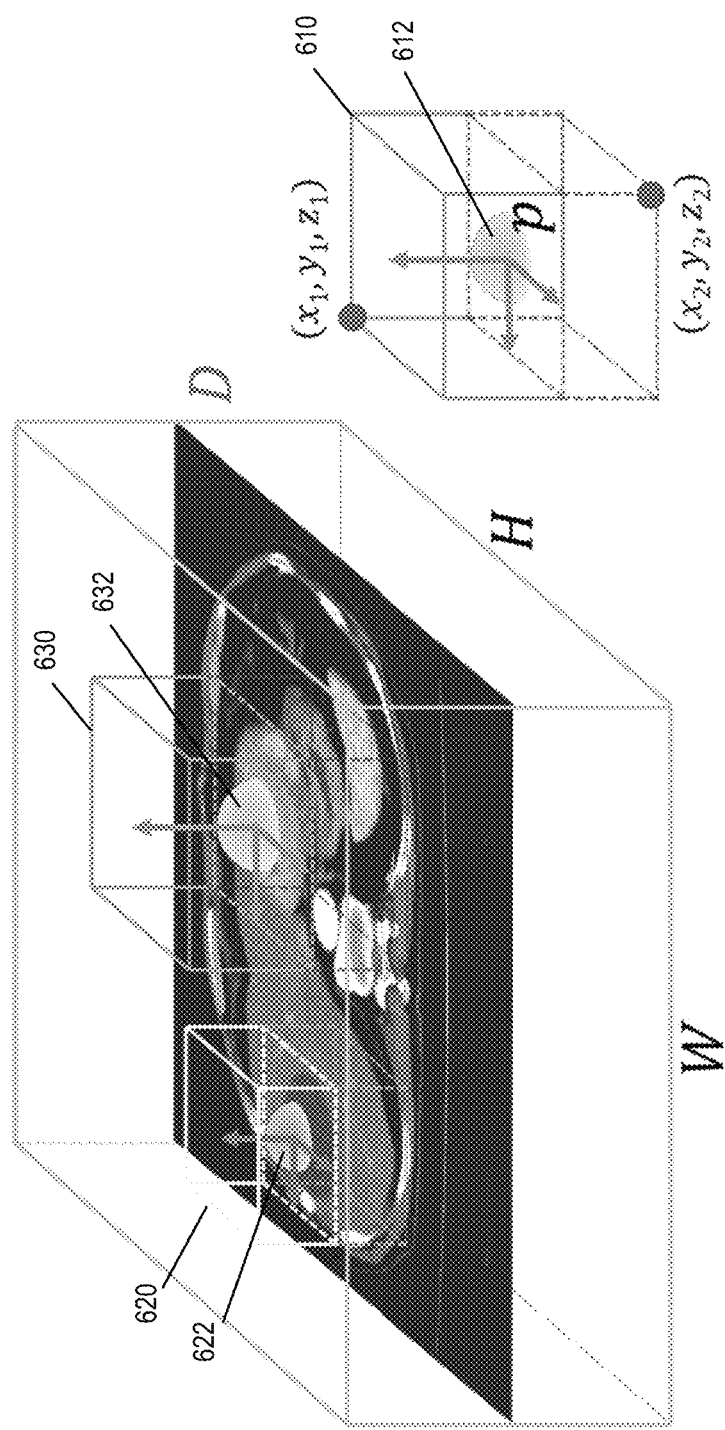
FIG. 6 illustrates exemplary 3D bounding boxes enclosing candidate tumor sites generated by a 3D detector, according to embodiments of the disclosure.

As shown in FIG. 1, primary tumor selector 150 may include 3D detector 120, key slice filter 130, and primary tumor slice filter 140. 3D detector 120 may be configured to detect one or more candidate tumors from 3D medical images 112. 3D detector 120 may be implemented using a 3D machine learning network, such as a 3D extension of CenterNet. In some embodiments, a one-stage and anchor-free CenterNet implementation may be adopted as it has both high performance and simplicity. In addition, 3D implementation may be adopted because it is more reliable and natural than the 2D variant. The CenterNet-based 3D detector 120 may follow a fully convolutional network (FCN) pipeline. The primary output of 3D detector 120 may include a 3D heatmap:

$$\hat{Y} \in [0,1]^{\frac{W}{R} \times \frac{H}{R} \times \frac{D}{R} \times C}$$

where C indicates the number of candidate classes, R is the down-sampling factor of the prediction, and W, H, D indicate the width, height, and depth, respectively, of the 3D medical image under detection, as shown in FIG. 6. The heatmap should equal to 1 at tumor centers and 0 otherwise. As FCN backbone, a stacked Hourglass-104 network in the original 2D CenterNet formulation is extended to a 3D variant. For example, while the ground truth of a 3D target center point can be modeled as a 3D Gaussian kernel, a non-isotropic Gaussian kernel may be used because medical images are typically non-isotropic (e.g., the physical voxel spacing in D, e.g., 5 mm, is normally larger than that in W and H, e.g., 1 mm). The non-isotropic Gaussian kernel $Y_{xyzc}$ can be represented as follows:

$$Y_{xyzc} = \exp\left(-\frac{\left(\frac{x-\tilde{p}_x}{\gamma_x}\right)^2 + \left(\frac{y-\tilde{p}_y}{\gamma_y}\right)^2 + \left(\frac{z-\tilde{p}_z}{\gamma_z}\right)^2}{2\sigma_p^2}\right)$$

where $\tilde{p}_x$, $\tilde{p}_y$, and $\tilde{p}_z$ are the down-sampled target center points $$\tilde{p} = \left\lfloor \frac{p}{R} \right\rfloor$$

and $\sigma_p$ is the kernel standard deviation. $\gamma_x$, $\gamma_y$, and $\gamma_z$ are the resolution coefficients to compensate for resolution differences. The corresponding pixel regression loss $L_k$ can be represented as follows:

$$L_k = \frac{-1}{N} \sum_{xyzc} \begin{cases} (1-\hat{Y}_{xyzc})^\alpha \log(\hat{Y}_{xyzc}) & \text{if } Y_{xyzc}=1 \\ (1-Y_{xyzc})^\beta (\hat{Y}_{xyzc})^\alpha \log(1-\hat{Y}_{xyzc}) & \text{otherwise} \end{cases}$$

where $\alpha$ and $\beta$ are hyper-parameters of the focal loss, and N is the number of key points in the image. In some embodiments, $\alpha=2$ and $\beta=4$ are chosen as exemplary hyper-parameters. The $l_1$-norm offset prediction loss $L_{off}$ can be represented as follows:

$$L_{off} = \frac{1}{N} \sum_p \left| \hat{O}_{\tilde{p}} - \left(\frac{p}{R} - \tilde{p}\right) \right|$$

where local offset $$\hat{O} \in R^{\frac{W}{R} \times \frac{H}{R} \times \frac{D}{R} \times 2}.$$

FIG. 6 illustrates exemplary 3D bounding boxes enclosing candidate tumor sites generated by 3D detector 120, according to embodiments of the disclosure. As shown in FIG. 6, 3D bounding box 610 can be defined by its two opposite vertices as $(x_1, y_1, z_1, x_2, y_2, z_2)$. The center point 612 can be modeled as $$p = \left(\frac{x_1+x_2}{2}, \frac{y_1+y_2}{2}, \frac{z_1+z_2}{2}\right).$$

The true bounding box size s is computed as $s=(x_2-x_1, y_2-y_1, z_2-z_1)$. For a predicted bounding box $\hat{s}$, the same L1 loss at the center point is calculated as follows:

$$L_{size} = \frac{1}{N} \sum_{k=1}^{N} \|\hat{s}_k - s_k\|_1$$

Bounding boxes 620 and 630 and their respective center points 622 and 632 can be similarly modeled.

The three loss functions ($L_k$, $L_{off}$, $L_{size}$) can be combined to set the overall loss function, which may be used to detect candidate tumors from 3D medical images 112 by, for example, minimizing the overall loss function. In some embodiments, a 3D bounding box for each candidate tumor may be determined, where each 3D bounding box may enclose the corresponding candidate tumor. As shown in FIG. 6, bounding boxes 620 and 630 each enclose their respective tumors, which are represented by Gaussian kernels (shown as blobs) located at the center points of the respective tumors. In some embodiments, an FCN-based liver segmentation may be performed (e.g., the segmentation network can be trained from public data) to create a liver mask, which may be used to crop the 3D medical images to reduce the amount of data for downstream processing. In some embodiments, resampling of the cropped region may be performed to further reduce and/or normalize the size of the image (e.g., sizing the region to be 176×256×48 or other suitable sizes).

As describe above, 3D detector 120 may be implemented by a learnable network or model, which can be trained using training data. In some embodiments, 3D detector 120 may be trained using public training datasets. In some embodiments, as shown in FIG. 1, 3D detector 120 may be trained by curated training data set 172. As will be discussed in greater detail below, curated training data set 172 may be generated by data curator 170 by harvesting large-scale hospital medical image data using a semi-automatic workflow. The abundance of features and information contained in curated training data set 172 can significantly enhance the performance of 3D detector 120 in the detection and localization of candidate tumors and generation of 3D bounding boxes from 3D medical images 112.

After 3D detector 120 detects candidate tumors in 3D medical images 112, the candidate tumors may be indicated by 3D bounding boxes enclosing the candidate tumors, as shown in medical images 122, which include the 3D bounding boxes. In some embodiments, multiple candidate tumors (e.g., indicated by their respective 3D bounding boxes) are detected (e.g., 10 candidate tumors) for each set of 3D multi-phase CT images. One or more of these candidate tumors may overlap with primary tumor(s). However, some candidate tumors may likely overlap with false positives, e.g., blood vessels, or non-significant lesions such as cysts. Key slice filter 130 and primary tumor slice filter 140 may be implemented to filter out these non-primary candidate tumors.

In some embodiments, SaDT classifier 160 may have better performance to classify tumors in 2D. Therefore, the filtering performed by key slice filter 130 and primary tumor slice filter 140 can be configured to process and output 2D images (e.g., slices) to SaDT classifier 160. For example, key slice filter 130 may determine the key slice (or key slices with multi-phase images) 132 for each candidate tumor from 3D medical images 122. Primary tumor slice filter 140 may then select the primary tumor from the candidate tumors based on their respective key slice(s) 132 and provide the key slice(s) 142 of the selected primary tumor to SaDT classifier 160 for classification.

Figure 7:
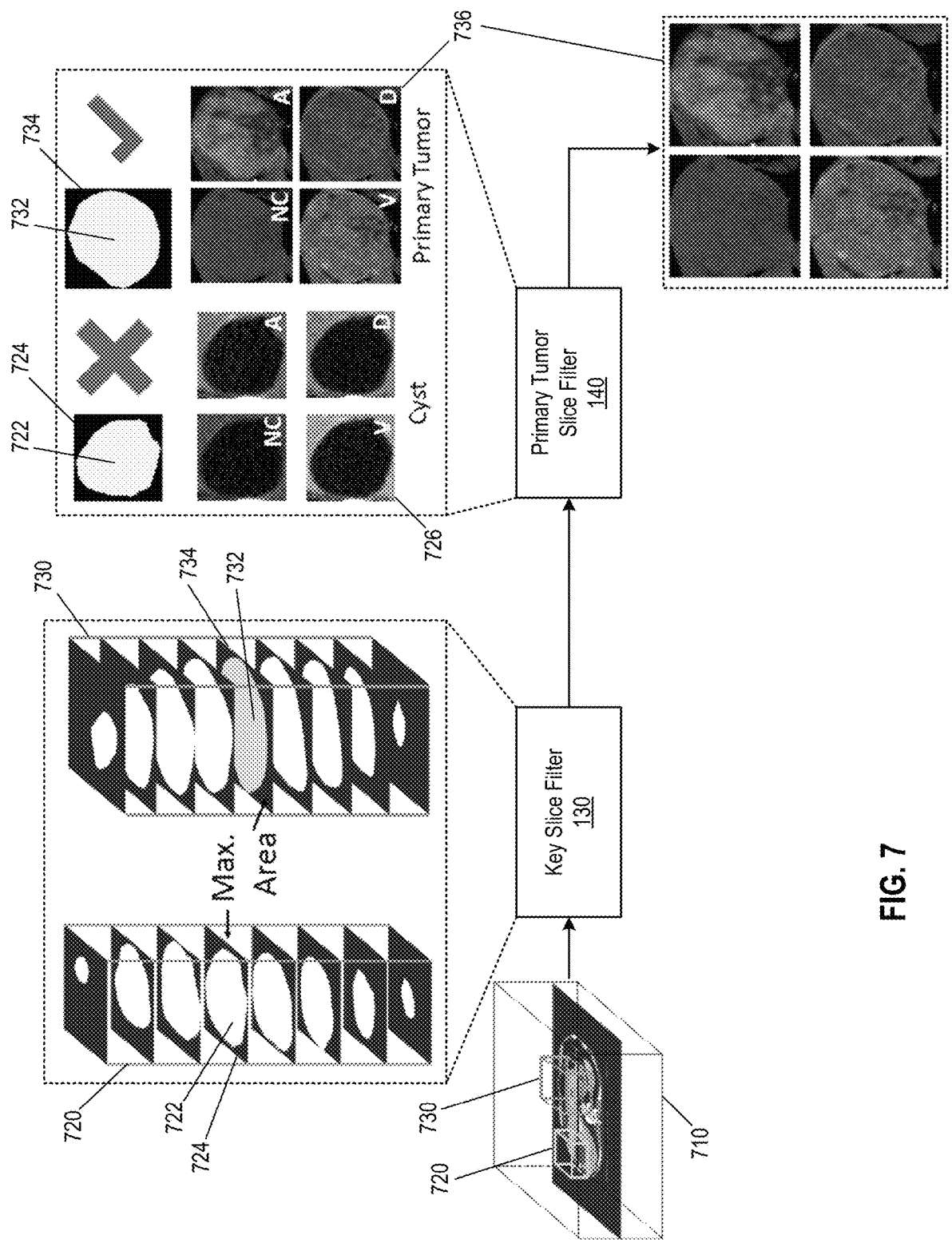
FIG. 7 illustrates an exemplary workflow of selecting a primary ROI based on key slice filtering, according to embodiments of the disclosure.

FIG. 7 illustrates an exemplary workflow of selecting a primary ROI (e.g., tumor) based on key slice filtering, according to embodiments of the disclosure. As shown in FIG. 7, 3D medical image 710 may be part of a multi-phase CT image (e.g., one of the four phases: non-contrast (NC), arterial (A), venous (V), and delayed (D), as discussed above). For ease of illustration, key slice filtering will be described with respect to a single phase, such as 3D medical image 710, as images in other phases can be processed in a similar manner. In addition, while 3D medical image 710 includes multiple slices, only one slice is shown in 3D medical image 710 for ease of illustration. Two 3D bounding boxes 720 and 730 are shown in 3D medical image 710. As described above, 3D bounding boxes 720 and 730 may each enclose a candidate tumor detected by 3D detector 120. 3D medical image 710 can be input into key slice filter 130, which in turn may determine a key slice for each of the candidate tumors enclosed by 3D bounding box 720 or 730. For example, key slice filter 130 may segment each candidate tumor in the corresponding 3D bounding box to separate a cross-section of that candidate tumor from its surroundings in each of the multiple slices of 3D medical image 710. As shown in FIG. 7, in bounding box 720, key slice filter 130 may segment a cross-section 722 of the enclosed candidate tumor from its surroundings in a slice 724, and segment other cross-sections from their respective surroundings in other slices. Similarly, in bounding box 730, key slice filter 130 may segment a cross-section 732 of the enclosed candidate tumor from its surroundings in a slice 734, and segment other cross-sections from their respective surroundings in other slices. The segmentation may be performed using a learnable segmentation network, such as a binary tumor segmentation network trained using public datasets, labeled multi-phase CT scans, and/or curated training data set 172 (as shown in FIG. 1, where curated training data set 172 can be used to train key slice filter 130). For example, a 2.5D segmentation head of the MULAN lesion detector may be adopted. Advantages of this lesion detector include: 1) it is pretrained on DeepLesion and should possess features with high lesion affinity; and 2) the 2.5D segmentation allows incorporation of sufficient background context without down-sampling or compromising the resolution.

After segmentation, key slice filter 130 may select, for each candidate tumor or in each bounding box, a 2D slice in which the corresponding cross-section has the largest area as the key slice for that candidate tumor. For example, among the cross-sections segmented in bounding box 720, cross-section 722 may have the largest area that is predicted by the segmentation network to be part of the candidate tumor enclosed by bounding box 720. Accordingly, slice 724 in which cross-section 722 is located may be selected as the key slice for the candidate tumor enclosed by bounding box 720. Similarly, among the cross-sections segmented in bounding box 730, cross-section 732 may have the largest area that is predicted by the segmentation network to be part of the candidate tumor enclosed by bounding box 730. Therefore, slice 734 in which cross-section 732 is located may be selected as the key slice for the candidate tumor enclosed by bounding box 730.

After the key slice is selected for each candidate tumor, the key slices can be input into primary tumor slice filter 140, which may separate primary tumor(s) from non-primary tumor(s). For example, a classification operation may be performed using a learnable image-based classifier to classify the candidate tumors into a first group including primary tumor(s) and a second group including non-primary tumor(s). In some embodiments, an appearance-based convolutional neural network (CNN) can be used as the classifier. In some embodiments, a texture-based classifier, such as SaDT 160 shown in FIG. 1, can be used to perform the classification. The classifier can be trained using, for example, public datasets, data generated from the key slice filtering process, and/or curated training data set 172 (as shown in FIG. 1, where curated training data set 172 can be used to train primary tumor slice filter 140). The data curation performed by data curator 170 and key slice filtering can be viewed as hard-negative mining and hard-negative filtering, respectively. As shown in FIG. 7, primary tumor slice filter 140 may perform classification on multi-phase CT images to separate primary tumor (shown in images 736) from non-primary tumor, such as cyst (shown in images 726), based on their respective key slices 734 and 724. In this way, primary tumor(s) can be selected based on the corresponding key slice(s), while non-primary tumor(s) can be filtered out based on the corresponding key slice(s). The output of primary tumor slice filter 140 may include the 2D key slice (or key slices when multi-phase medical images are used) of the primary tumor (e.g., key slices 736) resulting from the classification process.

Returning to FIG. 1, key slice(s) 142 (e.g., similar to key slices 736) of a selected primary tumor may be generated by primary tumor slice filter 140. Key slice(s) 142 may also be viewed as the output of primary tumor selector 150. SaDT classifier 160 may receive key slice(s) 142 and perform classification to classify the primary tumor into one of several categories. For example, FIG. 1 shows that SaDT classifier 160 can classify the primary tumor into one of four characterization results 161, including HCC, ICC, benign (e.g., including hemangioma, focal nodular hyperplasia, and adenoma), and metastasis. It is understood that the number of categories may be preset or adjusted in a system described herein. For example, fewer or more categories may be used in other implementations.

In some embodiments, SaDT classifier 160 may be implemented in 2D as the high inter-slice thickness of most CTs (e.g., 5 mm) may be too coarse to capture texture in that third dimension. For example, SaDT classifier 160 may be based on a 2D deep texture learning workflow, adapting and enhancing a DeepTEN model to create a SaDT network. Texture modeling may include counting, or soft-counting, codewords found in a set of visual descriptors. The visual descriptors, $F=\{f_1, \ldots, f_M\}$, can be generated from features of an encoding FCN, where M is the number of spatial locations in an activation map. The residuals of each feature compared to a set of K codewords, $C=\{c_1, \ldots, c_K\}$, can then be computed as follows:

$$r_{ik} = f_i - c_k$$

where $i=1, \ldots, M$ and $k=1, \ldots, K$. In some embodiments, the codewords may be fixed. In other embodiments, the codewords can be learned.

The set of all M×K residuals can be aggregated into a global size K feature describing the overall texture. Before aggregation, each residual may be assigned a weight. The weights can be computed based on a soft-assignment method. For example, in an exemplary soft-assignment method, the weight $a_{ik}$ of each residual $r_{ik}$ may be calculated using a softmax function as follows:

$$a_{ik} = \frac{\exp(-s_k \|r_{ik}\|^2)}{\sum_{j=1}^{K} \exp(-s_j \|r_{ij}\|^2)}$$

where $s_k$ is the smoothing factor for each cluster center $c_k$. The smoothing factors can also be designed as learnable parameters, which may be updated during the training procedure. In some embodiments, the soft-assignment method may be advantageous over a hard-assignment method, which only assigns a single fixed weight to each residual, thus making the process non-differentiable.

With the residuals and their weights, a set of features F can be encoded into a global feature E (e.g., a vector having K elements) by aggregating the weighted residuals together, where the global feature E indicates an overall texture. To account for the spatial variations caused by heterogeneity in tumor size across different cases, a spatial adaptive aggregation may be used to calculate the elements of global feature E:

$$e_k = \sum_{i=1}^{M} a_{ik} r_{ik} \delta_i$$

where each spatially adaptive factor $\delta_i$ is a binary value (e.g., 0 or 1), indicating if the corresponding weighted residual should be aggregated. In some embodiments, $\delta_i$ can be a tumor mask generated using the segmentation network of key slice filter 130. After aggregation, the final output vector can be normalized using an $l_2$-norm. In some embodiments, the same weighted focal-loss (e.g., $\gamma=2$) may be used as that used in the classification loss function to reconcile the overfitting to the dominating class. In some embodiments, the weights may be set to 5 for HCC, 2 for metastasis, and 1 for remaining classes. It is noted that other weight values may also be used. A stochastic gradient descent (SGD) optimizer with a proper learning rate (e.g., learning rate=0.004) can be used as well.

Figure 8:
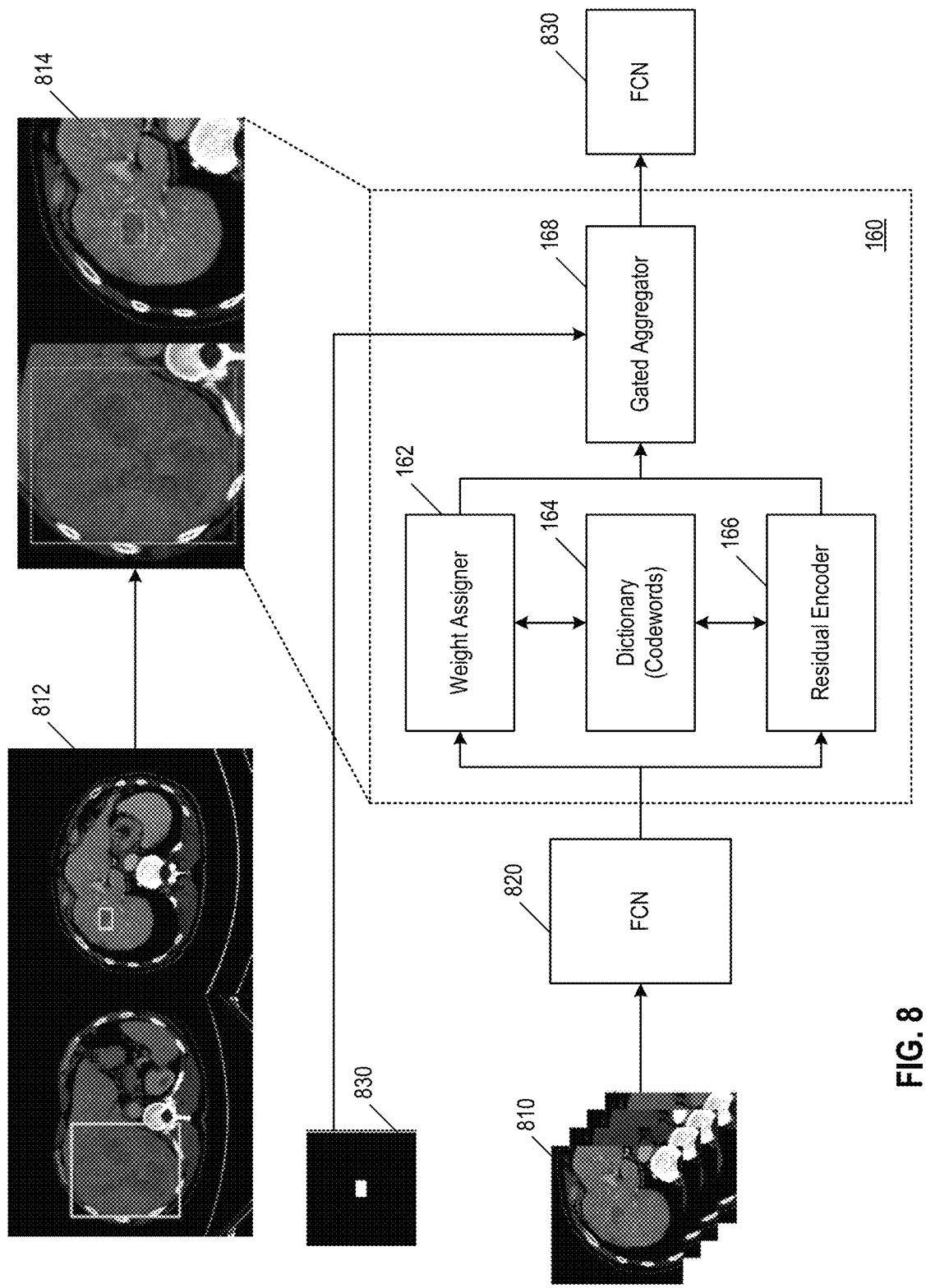
FIG. 8 illustrates an exemplary classifier for characterizing tumors, according to embodiments of the disclosure.

FIG. 8 illustrates an exemplary implementation of SaDT classifier 160 for characterizing tumors, according to embodiments of the disclosure. As shown in FIG. 8, key slices 810 of multi-phase medical images corresponding to a primary tumor may be input into an FCN 820, which may generate visual descriptors F indicating features in the key slices. Visual descriptors F may be received by SaDT classifier 160, which may include a weight assigner 162, a dictionary 164 that contains codewords, a residual encoder 166, and a gated aggregator 168. Residual encoder 166 may determine residuals $r_{ik}$ by comparing visual descriptors F with a set of codewords C in dictionary 164, as discussed above. Weight assigner 162 may assign a weight $a_{ik}$ to each residual. The weights may be determined according to the softmax function discussed above, which uses a learnable smoothing factor $s_k$ for each cluster center. After weight assignment, the weight residuals may be input to gated aggregator 168 for aggregation to generate a global feature E indicating the overall texture. Gated aggregator 168 may apply a spatially adaptive factor $\delta_i$ based on a tumor mask 830 to each of the weighted residuals to generate a spatially adaptive weighted residual. Gated aggregator 168 may then aggregate the spatially adaptive weighted residuals to generate the global feature E. The spatial adaptive effect can be illustrated by images 812 and 814. Image 812 shows heterogeneous liver tumors, and image 814 shows that after application of the spatial adaptive factor the intensity of the surroundings is kept intact. The global feature E may be input to an FCN 830, which may perform normalization and classification of the primary tumor. It is noted that FCN 820 and/or FCN 830 may or may not be part of SaDT classifier 160.

Figure 2:
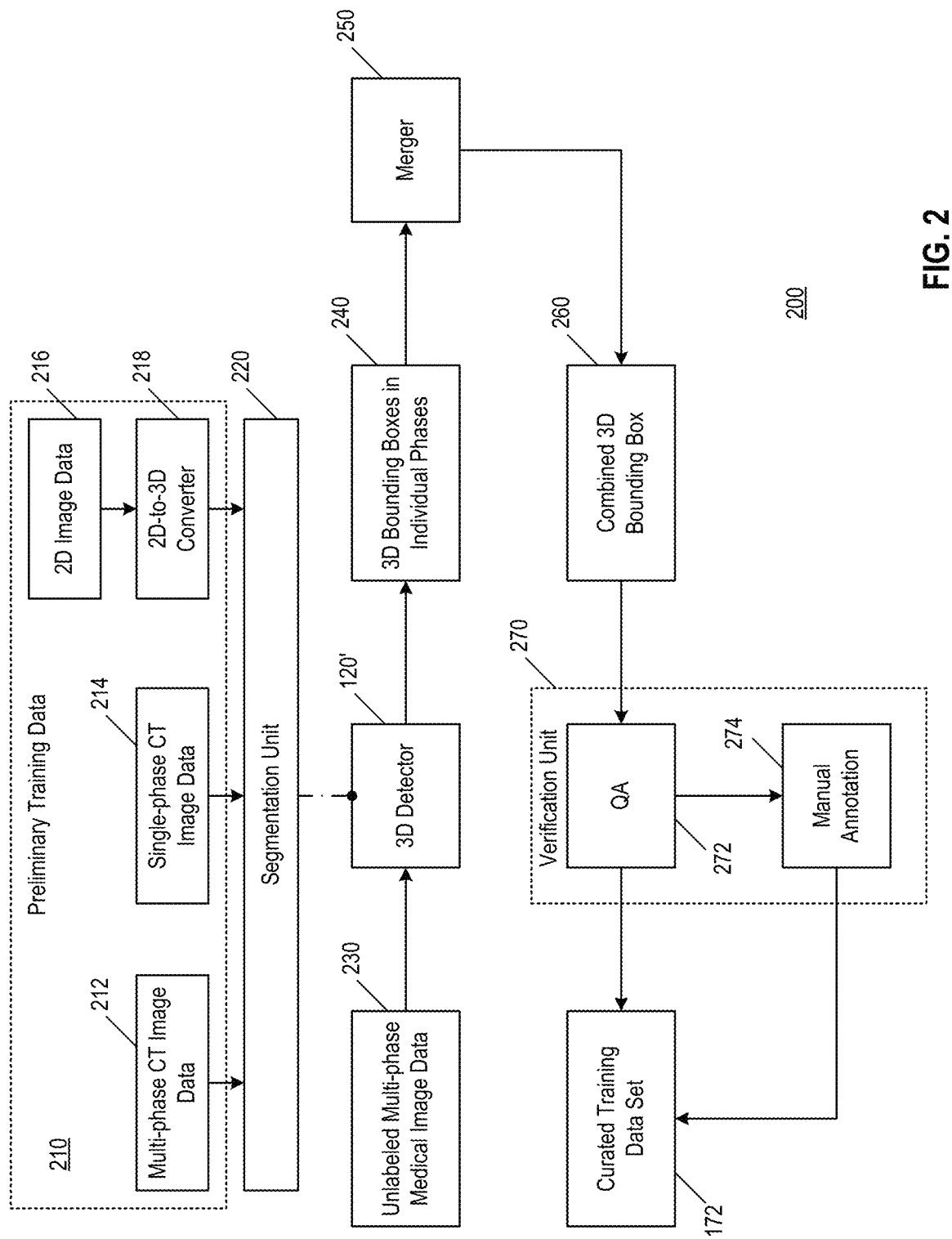
FIG. 2 illustrates an exemplary data curation system, according to embodiments of the disclosure.

FIG. 2 illustrates an exemplary data curation system 200, according to embodiments of the disclosure. Data curation system 200 may include an exemplary implementation of data curator 170 shown in FIG. 1. As shown in FIG. 2, data curation system 200 may harvest large-scale unlabeled medical image datasets, such as hospital CT scans, to generate curated training data set 172 including annotations to pathologically confirmed tumors. For example, unlabeled multi-phase medical image data 230 may contain unlabeled multi-phase CT image data, which may only have image-level ground truth information (e.g., pathologically confirmed tumor(s)), but lack annotations, such as bounding boxes, to the specific location(s) of the tumor(s). To locate the tumor(s), a 3D detector 120' may be used. In some embodiments, 3D detector 120' may be the same as 3D detector 120, but not yet trained by curated training data set 172. Instead, 3D detector 120' may be preliminarily trained using a preliminary training data set 210, which may contain, for example, multi-phase CT image data 212, single-phase CT image data 214, and/or 2D image data 216. 2D image data 216 may be converted to 3D image data by a 2D-to-3D converter 218. Preliminary training data set 210 may be segmented by a segmentation unit 220 to separate, for example, liver from other body parts. The segmented preliminary training data set can then be used to preliminarily train 3D detector 120'. To harmonize the different channel/phase numbers, multi-phase CT image data 212 can be input as multiple single-phase CT image data. For example, all phases of the multi-phase CT image data can be input sequentially as individual phases.

After 3D detector 120' is preliminarily trained, 3D detector 120' can be applied to unlabeled multi-phase medical image data 230 to obtain 3D bounding boxes 240 of predicted tumors in each individual phase. A merger 250 can then merge corresponding 3D bounding boxes obtained in individual phases into a combined 3D bounding box 260 for each predicted tumor. After that, the detection results may undergo a quality assurance process 272. For example, each combined 3D bounding box may be rendered together with its corresponding multi-phase CT images in a grid layout. A rapid mouse-click-based QA process can be carried out to verify or reject the detected 3D bounding boxes. If a 3D bounding box passes the QA process 272, the 3D bounding box along with its corresponding medical images may be added to curated training data set 172. Otherwise, a manual annotation process 274 can be carried out to manually annotate the tumor(s). In some embodiments, QA process 272 and manual annotation process 274 may be collectively carried out by a verification unit 270. The semi-automatic data curation system 200 can reduce the annotation time by an order compared to a fully manual annotation counterpart, thereby greatly expanding the space of available training data.

Figure 3:
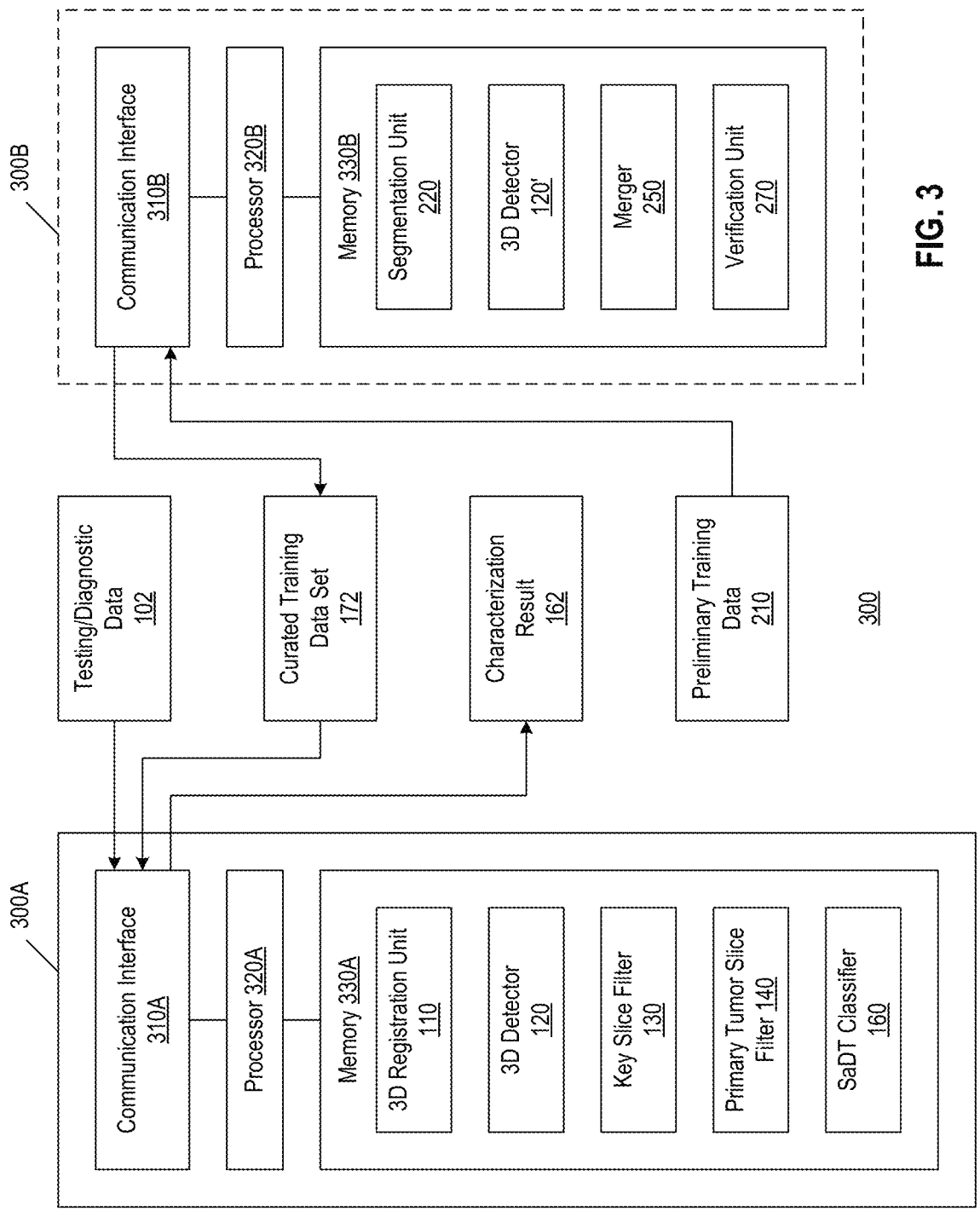
FIG. 3 illustrates an exemplary computer system for implementing the tumor characterization system and the data curation system shown in FIGS. 1 and 2, respectively, according to embodiments of the disclosure.

FIG. 3 illustrates an exemplary computer system 300 for implementing the tumor characterization system and the data curation system shown in FIGS. 1 and 2, respectively, according to embodiments of the disclosure. As shown in FIG. 3, computer system 300 may include a sub-system 300A for characterizing tumors and a sub-system 300B for generating curated training data set 172. In some embodiments, sub-systems 300A and 300B may be the same system or at least share some components of one system. In some embodiments, sub-systems 300A and 300B may be different systems. In either case, sub-systems 300A and 300B may have similar functional components. For example, both sub-systems 300A and 300B may include a communication interface (310A and 310B, respectively), at least one processor (320A and 320B, respectively), and a memory (330A and 330B, respectively). Accordingly, sub-system 300A will be described as a representative sub-system, while descriptions of similar components in sub-system 300B are omitted.

Communication interface 310A may include any suitable wired and wireless; networked and point-to-point; hardware, middleware, and software components that facilitate data communication and/or information exchange between sub-system 300A and any one of the devices storing/displaying testing/diagnostic data 102, curated training data set 172, and/or characterization result 161. For example, communication interface 310A may include an LAN network adaptor, a WLAN adaptor, a WAN adaptor, a fiber network adaptor, a telecommunication network adaptor, or the like. In some embodiments, communication interface 310A may include I/O devices such as a display, a printer, a keyboard, a mouse, a touchpad, a touchscreen, a stylus pen, or the like. Communication interface 310A may receive testing/diagnostic data 102 and transmit to processor 320A for characterization. Communication interface 310A may receive curated training data set 172 and transmit to processor 320A for training one or more machine learning networks. Communication interface 310A may receive tumor characterization information and transmit to an outside destination as characterization result 161.

Communication interface 310B may be similar to communication interface 310A structurally but may be configured to handle different data. For example, communication interface 310B may receive preliminary training data 210 and transmit to processor 320B to preliminarily train 3D detector 120'. Communication interface 310B may also receive data curation output from processor 320B and output as curated training data set 172.

Processor 320A may include any suitable microprocessors, central processing units (CPUs), graphic processing units (GPUs), or the like. Processor 320A may be communicatively coupled to communication interface 310A and memory 330A. Memory 330A may include a RAM, a ROM, a hard drive, a flash drive, an SSD, or any suitable data storage devices. Memory 330A may store computer-readable instructions that can be executed by processor 320A. The computer-readable instructions, when executed by processor 320A, may perform operations that implement one or more functions described above in connection with FIGS. 1, 2, and 4-8. For example, memory 330A may store instructions for implementing 3D registration unit 110, 3D detector 120, key slice filter 130, primary tumor slice filter 140, and/or SaDT classifier 160. Similarly, memory 330B of sub-system 300B may store instructions for implementing segmentation unit 220, 3D detector 120', merger 250, and/or verification unit 270.

Figure 9:
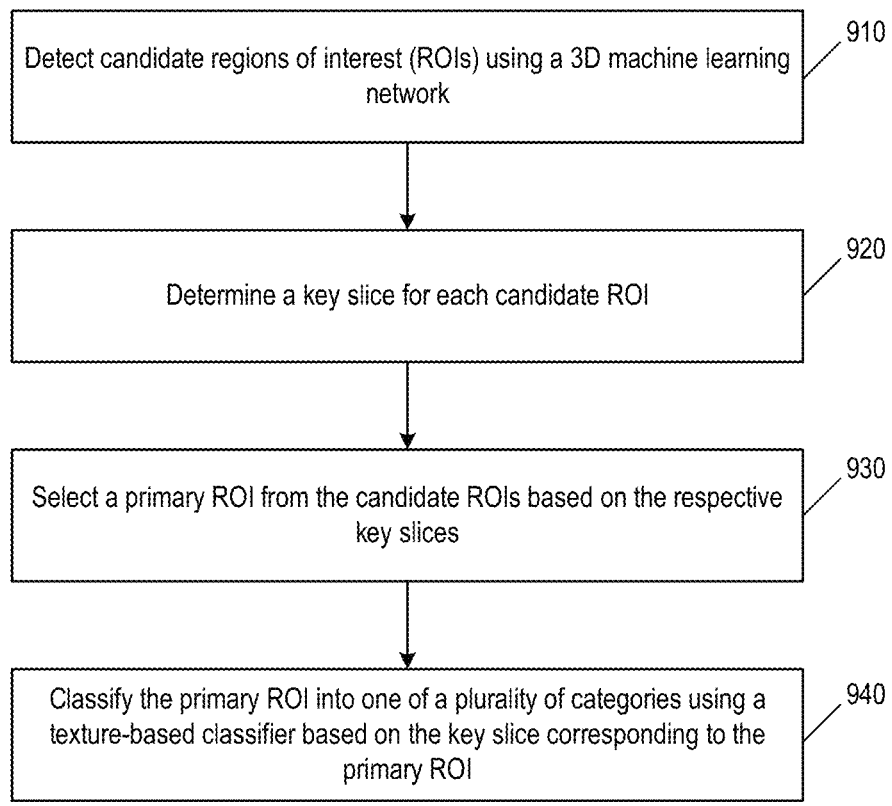
FIG. 9 is a flowchart of an exemplary method for characterizing a tumor, according to embodiments of the disclosure.

FIG. 9 illustrates a flowchart of an exemplary method 900 for characterizing an ROI (e.g., a tumor), according to embodiments of the disclosure. Method 900 may be performed by system 100, which can be implemented by sub-system 300A. It is to be appreciated that some of the steps may be optional. Further, some of the steps may be performed simultaneously, or in a different order than that shown in FIG. 9.

Referring to FIG. 9, method 900 may include steps 910-940. In step 910, one or more candidate ROIs may be detected using a 3D machine learning network, such as 3D detector 120. In step 920, key slice filter 130 may determine a key slice for each candidate ROI. In step 930, primary tumor slice filter 140 may select a primary ROI from the candidate ROIs based on the respective key slices. In step 940, a texture-based classifier, such as SaDT classifier 160, may classify the primary ROI into one of a plurality of categories (e.g., HCC, ICC, benign, and metastasis) based on the key slice corresponding to the primary ROI. Detailed descriptions of steps 910-940 are provided above in connection with system 100 and are therefore not repeated.

Figure 10:
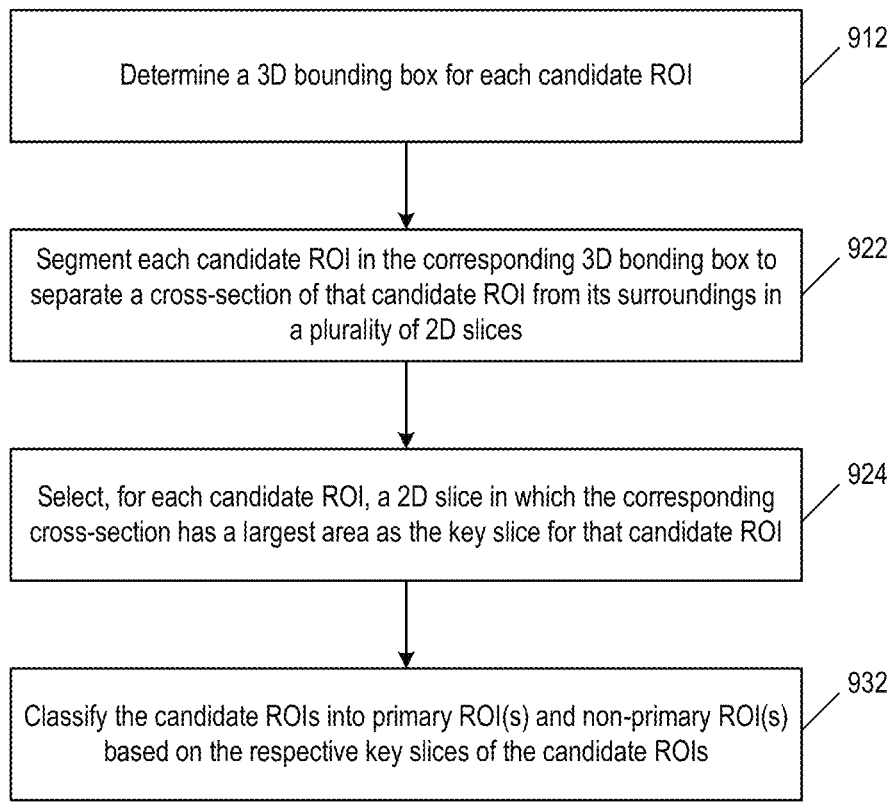
FIG. 10 is a flowchart of an exemplary method for selecting a primary tumor from candidate tumors, according to embodiments of the disclosure.

FIG. 10 is a flowchart of an exemplary method for selecting a primary tumor from candidate tumors, according to embodiments of the disclosure. The method shown in FIG. 10 may be performed by system 100, which can be implemented by sub-system 300A. It is to be appreciated that some of the steps may be optional. Further, some of the steps may be performed simultaneously, or in a different order than that shown in FIG. 10.

Referring to FIG. 10, the method may include steps 912, 922, 924, and 932. Step 912 may be a sub-step of step 910. In step 912, 3D detector 120 may determine a 3D bounding box for each candidate ROI. Detailed descriptions of step 912 are provided above in connection with system 100 and FIG. 6, and are therefore not repeated. Steps 922 and 924 may be sub-steps of step 920. In step 922, key slice filter 130 may segment each candidate ROI in the corresponding 3D bonding box to separate a cross-section of that candidate ROI from its surroundings in a plurality of 2D slices. In step 924, key slice filter 130 may select, for each candidate ROT, a 2D slice in which the corresponding cross-section has a largest area as the key slice for that candidate ROI. Detailed descriptions of steps 922 and 924 are provided above in connection with system 100 and FIG. 7, and are therefore not repeated. Step 932 may be a sub-step of step 930. In step 932, primary tumor slice filter 140 may classify the candidate ROIs into a first group having the primary ROI(s) and a second group having the non-primary ROI(s) based on the respective key slices of the candidate ROIs. Detailed descriptions of step 932 are provided above in connection with system 100 and FIG. 7 and are therefore not repeated.

Figure 11:
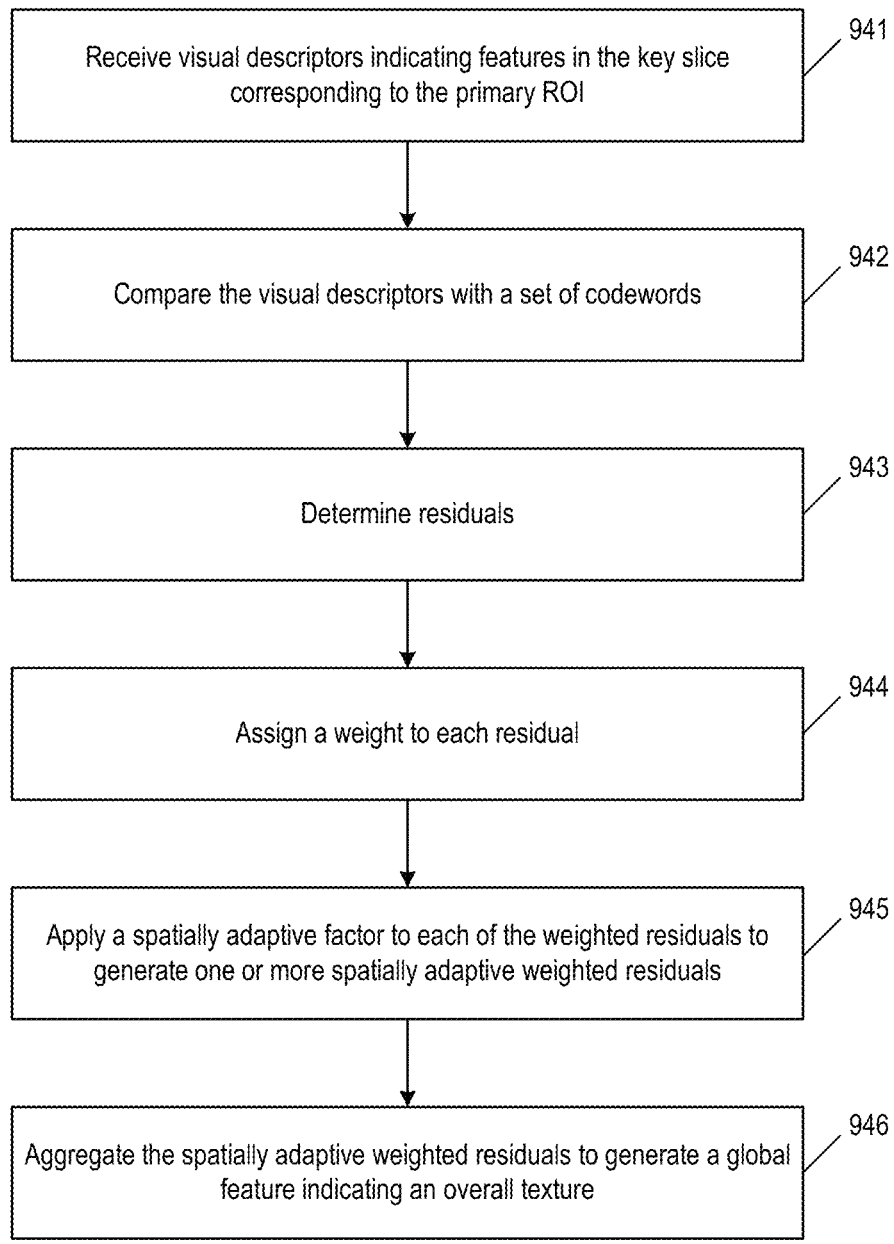
FIG. 11 is a flowchart of an exemplary method for classifying a tumor, according to embodiments of the disclosure.

FIG. 11 is a flowchart of an exemplary implementation of step 940 for classifying a tumor, according to embodiments of the disclosure. The method shown in FIG. 11 may be performed by system 100, which can be implemented by sub-system 300A. It is to be appreciated that some of the steps may be optional. Further, some of the steps may be performed simultaneously, or in a different order than that shown in FIG. 11.

Referring to FIG. 11, step 940 may further include sub-steps 941-946. In step 941, SaDT classifier 160 may receive visual descriptors indicating features in the key slice corresponding to the primary ROI. In step 942, SaDT classifier 160 may compare the visual descriptors with a set of codewords. In step 943, SaDT classifier 160 may determine residuals based on the comparison. In step 944, SaDT classifier 160 may assign a weight to each residual. In step 945, SaDT classifier 160 may apply a spatially adaptive factor to each of the weighted residuals to generate one or more spatially adaptive weighted residuals. In step 946, SaDT classifier 160 may aggregate the spatially adaptive weighted residuals to generate a global feature indicating an overall texture. Detailed descriptions of steps 941-946 are provided above in connection with system 100 and FIG. 8, and are therefore not repeated.

Figure 12:
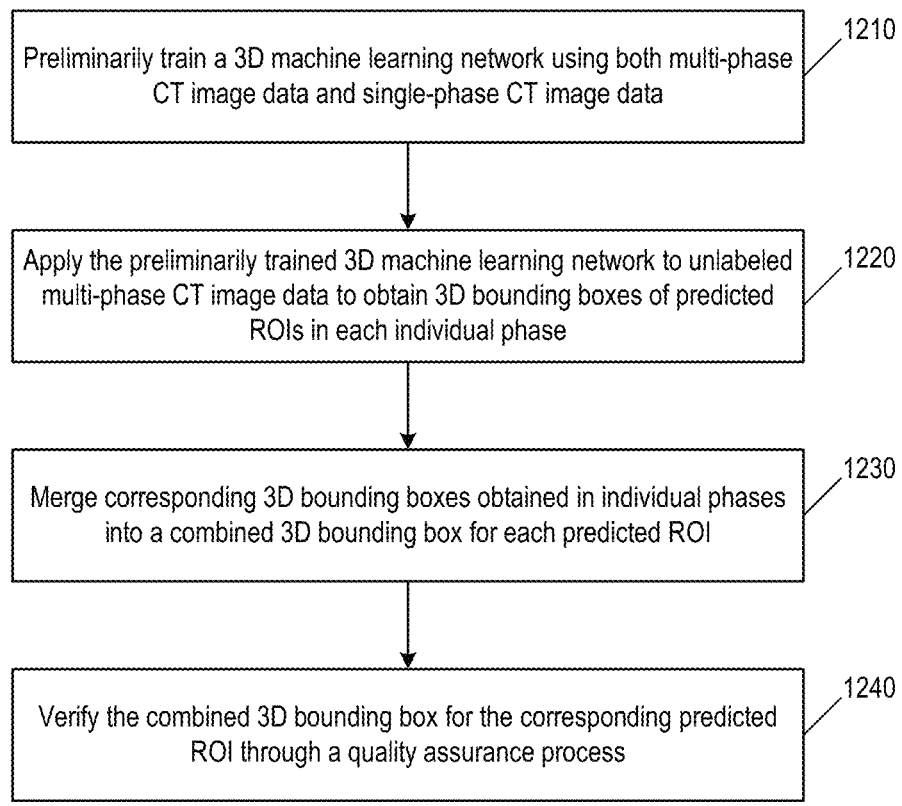
FIG. 12 is a flowchart of an exemplary method for data curation, according to embodiments of the disclosure.
Figure 13:
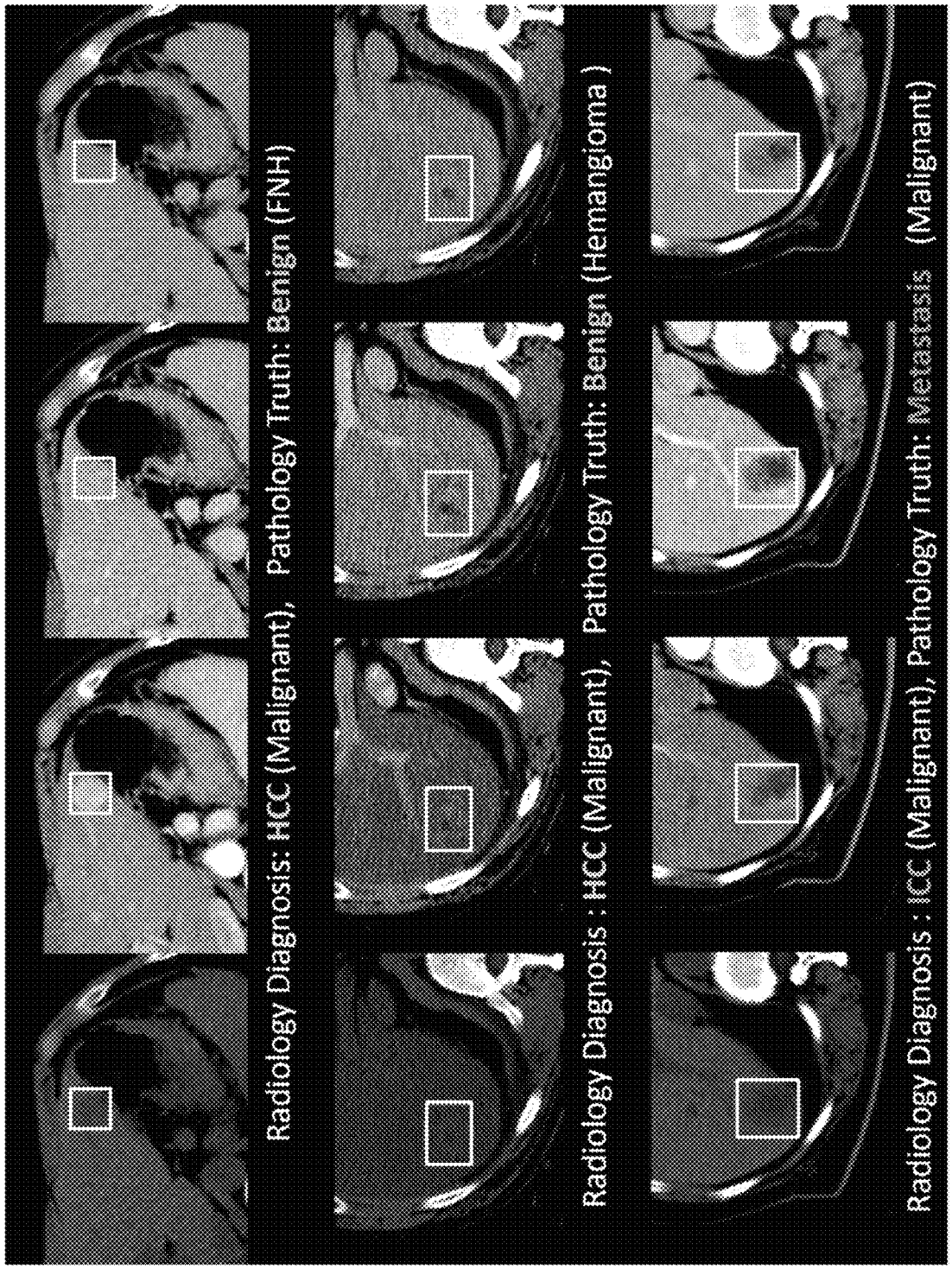
FIG. 13 illustrates exemplary misdiagnosis scenarios using state-of-the-art medical imaging-based liver cancer diagnosis systems.

FIG. 12 is a flowchart of an exemplary method 1200 for data curation, according to embodiments of the disclosure. Method 1200 may be performed by system 200, which may be implemented by sub-system 300B. It is to be appreciated that some of the steps may be optional. Further, some of the steps may be performed simultaneously, or in a different order than that shown in FIG. 12.

Referring to FIG. 12, method 1200 may include steps 1210-1240. In step 1210, 3D detector 120' may be preliminarily trained using both multi-phase CT image data and single-phase CT image data. 3D detector 120' may be a 3D machine learning network. In step 1220, the preliminarily trained 3D detector 120' may be applied to unlabeled multi-phase CT image data to obtain 3D bounding boxes of predicted ROIs in each individual phase. In step 1230, merger 250 may merge corresponding 3D bounding boxes obtained in individual phases into a combined 3D bounding box for each predicted ROI. In step 1240, the combined 3D bounding box for the corresponding predicted ROI may be verified through quality assurance process 272. Detailed descriptions of steps 1210-1240 are provided above in connection with system 200, and are therefore not repeated.

Another aspect of the disclosure is directed to a non-transitory computer-readable medium storing instructions that, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed systems. Other embodiments will be apparent to those skilled in the art from consideration of the specification and practice of the disclosed systems.

It is intended that the specification and examples be considered as exemplary only, with a true scope being indicated by the following claims and their equivalents.

The invention claimed is:

1. A system for characterizing a region of interest (ROI) in a medical image, comprising:
   a memory storing computer-readable instructions; and
   at least one processor communicatively coupled to the memory to execute the computer-readable instructions, wherein the computer-readable instructions, when executed by the at least one processor, cause the at least one processor to perform operations comprising:
      detecting one or more candidate ROIs from the medical image using a three-dimensional (3D) machine learning network;
      determining a key slice for each candidate ROI;
      selecting a primary ROI from the one or more candidate ROIs based on the respective key slices; and
      classifying the primary ROI into one of a plurality of categories using a texture-based classifier based on the key slice corresponding to the primary ROI, wherein the texture-based classifier is spatially adaptive with a set of spatially adaptive factors generated based on a tumor mask.

2. The system of claim 1, wherein the primary ROI comprises an image of a liver tumor.

3. The system of claim 1, wherein the plurality of categories comprise at least two from a group consisting of an intrahepatic cholangiocarcinoma (ICC), a hepatocellular carcinoma (HCC), a metastasis, and a benign tumor.

4. The system of claim 1, wherein the medical image comprises at least one image from a set of multi-phase Computed Tomography (CT) images.

5. The system of claim 1, wherein detecting the one or more candidate ROIs comprises:
   determining a 3D bounding box for each of the one or more candidate ROIs, wherein the 3D bounding box encloses the corresponding candidate ROI.

6. The system of claim 5, wherein determining the key slice comprises:
   segmenting each of the one or more candidate ROIs in the corresponding 3D bounding box to separate, in a plurality of two-dimensional (2D) slices of the medical image, a cross-section of that candidate ROI from its surroundings; and selecting, for each of the one or more candidate ROIs, a 2D slice of the medical image in which the corresponding cross-section has a largest area as the key slice for that candidate ROI.

7. The system of claim 1, wherein selecting the primary ROI comprises:
classifying, by an image-based classifier, the candidate ROIs into a first group comprising the primary ROI and a second group comprising one or more non-primary ROIs based on the respective key slices of the candidate ROIs.

8. The system of claim 1, wherein classifying the primary ROI into one of the plurality of categories comprises:
receiving a set of visual descriptors indicating features in the key slice corresponding to the primary ROI;
determining a set of residuals by comparing the set of visual descriptors with a set of codewords;
assigning a corresponding weight to each residual so that a set of weighted residuals is generated, wherein the corresponding weight is determined by a softmax function using learnable smoothing factors; and
aggregating the set of weighted residuals to generate a global feature indicating an overall texture based on the set of spatially adaptive factors.

9. The system of claim 8, wherein aggregating the set of weighted residuals to generate the global feature indicating the overall texture based on the set of spatially adaptive factors comprises:
applying a corresponding spatially adaptive factor from the set of spatially adaptive factors to each weighted residual to generate one or more spatially adaptive weighted residuals; and
aggregating the one or more spatially adaptive weighted residuals to generate the global feature indicating the overall texture.

10. The system of claim 1, wherein the 3D machine learning network is trained by a training data set comprising annotations to pathologically confirmed tumors, wherein at least part of the training data set is harvested from unlabeled medical image data.

11. The system of claim 10, wherein:
the unlabeled medical image data comprises unlabeled multi-phase Computed Tomography (CT) image data; and
at least part of the training data set is harvested from the unlabeled multi-phase CT image data by a data curation process comprising:
preliminarily training the 3D machine learning network using both multi-phase CT image data and single-phase CT image data, wherein the multi-phase CT image data are is input as multiple single-phase CT image data;
applying the preliminarily trained 3D machine learning network to the unlabeled multi-phase CT image data to obtain 3D bounding boxes of predicted ROIs in each individual phase;
merging corresponding 3D bounding boxes obtained in individual phases into a combined 3D bounding box for each predicted ROI; and
verifying the combined 3D bounding box for the corresponding predicted ROI through a quality assurance process.

12. The system of claim 1, wherein an output of the 3D machine learning network comprises a 3D heatmap comprising a first value at tumor centers and a second value at other locations.

13. A method for characterizing a region of interest (ROI) in a medical image, comprising:
detecting, by a processor, one or more candidate ROIs from the medical image using a three-dimensional (3D) machine learning network;
determining, by the processor, a key slice for each candidate ROI;
selecting, by the processor, a primary ROI from the one or more candidate ROIs based on the respective key slices; and
classifying, by the processor, the primary ROI into one of a plurality of categories using a texture-based classifier based on the key slice corresponding to the primary ROI, wherein the texture-based classifier is spatially adaptive with a set of spatially adaptive factors generated based on a tumor mask.

14. The method of claim 13, wherein detecting the one or more candidate ROIs comprises:
determining a 3D bounding box for each of the one or more candidate ROIs, wherein the 3D bounding box encloses the corresponding candidate ROI.

15. The method of claim 14, wherein determining the key slice comprises:
segmenting each of the one or more candidate ROIs in the corresponding 3D bounding box to separate, in a plurality of two-dimensional (2D) slices of the medical image, a cross-section of that candidate ROI from its surroundings; and
selecting, for each of the one or more candidate ROIs, a 2D slice of the medical image in which the corresponding cross-section has a largest area as the key slice for that candidate ROI.

16. The method of claim 13, wherein selecting the primary ROI comprises:
classifying, by an image-based classifier, the candidate ROIs into a first group comprising the primary ROI and a second group comprising one or more non-primary ROIs based on the respective key slices of the candidate ROIs.

17. The method of claim 13, wherein classifying the primary ROI into one of the plurality of categories comprises:
receiving a set of visual descriptors indicating features in the key slice corresponding to the primary ROI;
determining a set of residuals by comparing the set of visual descriptors with a set of codewords;
assigning corresponding a weight to each residual so that a set of weighted residuals is generated, wherein the corresponding weight is determined by a softmax function using learnable smoothing factors; and
aggregating the set of weighted residuals to generate a global feature indicating an overall texture based on the set of spatially adaptive factors.

18. The method of claim 17, wherein aggregating the set of weighted residuals to generate the global feature indicating the overall texture based on the set of spatially adaptive factors comprises:
applying a corresponding spatially adaptive factor from the set of spatially adaptive factors to each weighted residual to generate one or more spatially adaptive weighted residuals; and
aggregating the one or more spatially adaptive weighted residuals to generate the global feature indicating the overall texture.

19. The method of claim 13, wherein:
the 3D machine learning network is trained by a training data set comprising annotations to pathologically confirmed tumors, wherein at least part of the training data set is harvested from unlabeled medical image data;

the unlabeled medical image data comprises unlabeled multi-phase Computed Tomography (CT) image data; and at least part of the training data set is harvested from the unlabeled multi-phase CT image data by a data curation process comprising:

preliminarily training the 3D machine learning network using both multi-phase CT image data and single-phase CT image data, wherein the multi-phase CT image data are is input as multiple single-phase CT image data;

applying the preliminarily trained 3D machine learning network to the unlabeled multi-phase CT image data to obtain 3D bounding boxes of predicted ROIs in each individual phase;

merging corresponding 3D bounding boxes obtained in individual phases into a combined 3D bounding box for each predicted ROI; and verifying the combined 3D bounding box for the corresponding predicted ROI through a quality assurance process.

20. A non-transitory computer-readable medium storing instructions that, when executed by at least one processor, cause the at least one processor to perform a method for characterizing a region of interest (ROI) in a medical image, the method comprising:

detecting one or more candidate ROIs from the medical image using a three-dimensional (3D) machine learning network;

determining a key slice for each candidate ROI;

selecting a primary ROI from the one or more candidate ROIs based on the respective key slices; and classifying the primary ROI into one of a plurality of categories using a texture-based classifier based on the key slice corresponding to the primary ROI, wherein the texture-based classifier is spatially adaptive with a set of spatially adaptive factors generated based on a tumor mask.

\* \* \* \* \*